US006381351B1

(12) United States Patent
Powell

(10) Patent No.: US 6,381,351 B1
(45) Date of Patent: Apr. 30, 2002

(54) WEIGHTED INVERSE TOPOGRAPHY METHOD FOR DIGITAL X-RAY IMAGE DATA PROCESSING

(75) Inventor: Gregory F. Powell, Bear, DE (US)

(73) Assignee: Direct Radiography Corp., Newark, DE (US)

( * ) Notice: Subject to any disclaimer, the term of this patent is extended or adjusted under 35 U.S.C. 154(b) by 0 days.

(21) Appl. No.: 09/449,073

(22) Filed: Nov. 24, 1999

(51) Int. Cl.⁷ .................................................. G06K 9/00
(52) U.S. Cl. ...................................... 382/131; 250/455
(58) Field of Search ................................. 382/128, 129, 382/130, 131, 132, 264; 250/455

(56) References Cited

U.S. PATENT DOCUMENTS

| | | | |
|---|---|---|---|
| 4,599,742 A | 7/1986 | Kikuchi et al. ................ 378/99 |
| 4,661,986 A | 4/1987 | Adelson ....................... 382/41 |
| 4,674,125 A | 6/1987 | Carlson et al. ............... 382/49 |
| 4,698,843 A | 10/1987 | Burt et al. .................... 382/54 |
| 4,833,625 A | 5/1989 | Fisher et al. ................ 364/518 |
| 4,868,651 A | 9/1989 | Chou et al. .................. 358/111 |
| 4,914,295 A | 4/1990 | Shimura et al. ......... 250/327.2 |
| 5,029,226 A | 7/1991 | Klein et al. .................... 382/50 |
| 5,046,118 A | 9/1991 | Ajewole et al. .............. 382/51 |
| 5,151,947 A | 9/1992 | Nagatsuka et al. ............ 382/6 |
| 5,157,733 A | 10/1992 | Takeo et al. ................... 382/6 |
| 5,164,993 A | 11/1992 | Capozzi et al. ............... 382/6 |
| 5,260,871 A | 11/1993 | Goldberg ................ 364/413.02 |
| 5,268,967 A | 12/1993 | Jang et al. ...................... 382/6 |
| 5,313,066 A | 5/1994 | Lee et al. .............. 250/370.09 |
| 5,315,101 A | 5/1994 | Hughes et al. ........... 250/208.1 |
| 5,331,179 A * | 7/1994 | Lee et al. .................... 250/591 |
| 5,388,138 A | 2/1995 | Fujiwara ..................... 378/108 |
| 5,444,792 A * | 8/1995 | Grangeat et al. ............ 382/131 |
| 5,526,442 A * | 6/1996 | Baba et al. .................. 382/132 |
| 5,574,764 A | 11/1996 | Granfors et al. ........... 378/98.7 |
| 5,596,654 A | 1/1997 | Tanaka ....................... 382/168 |
| 5,606,587 A | 2/1997 | Barski et al. .................. 378/62 |
| 5,633,511 A | 5/1997 | Lee et al. .................... 250/587 |
| 5,675,624 A | 10/1997 | Relihan et al. ............. 378/98.7 |
| 6,118,892 A * | 9/2000 | Williams ..................... 382/132 |
| 6,130,958 A * | 10/2000 | Rohler et al. ............... 382/131 |
| 6,173,083 B1 * | 1/2001 | Aviash ........................ 382/260 |

FOREIGN PATENT DOCUMENTS

| | | | |
|---|---|---|---|
| WO | WO 98/37738 | 8/1998 | ............ H05G/1/64 |

OTHER PUBLICATIONS

"Automatic Setting Functions for Image Density and Range in the FCR System" by N. Nakajima, H. Takeo, M. Ishida, and T. Nagata. Fuji Computed Radiography Technical Review No. 3, pp. 1–23.

"The Laplacian Pyramid as a Compact Image Code" by Peter J. Burt and Edward H. Adelson. IEEE Transactions on Communications, vol. COM–31, No. 4, Apr. 1983, pp. 532–540.

* cited by examiner

*Primary Examiner*—Joseph Mancuso
*Assistant Examiner*—A Tabatabai
(74) *Attorney, Agent, or Firm*—Ratner & Prestia

(57) ABSTRACT

A method for displaying on a display medium an image corresponding to detected exposures of a plurality of pixels converted to a matrix having n rows and m columns of digital values. The method comprises creating a weighted, smoothed, subtracted matrix, adding the weighted, smoothed, subtracted matrix to the starting matrix to produce an enhanced matrix; and then using the digital values from the enhanced matrix to display an image. Preferably, a sampled submatrix of digital values having n/I rows and m/I columns is created from the starting matrix from which is compiled a weighted, smoothed, subtracted submatrix that is then extrapolated to create the weighted, smoothed, subtracted matrix. A program storage device for carrying out the method, a digital x-ray image data capture system, and a method of using the system of this invention are also claimed.

22 Claims, 7 Drawing Sheets

STANDARD EXAM-SPECIFIC PROCESSING

INVERSE TOPOGRAPHY

WEIGHTED INVERSE TOPOGRAPHY METHOD FOR DIGITAL X-RAY IMAGE DATA PROCESSING

FIELD OF THE INVENTION

This invention relates to a method for enhancing areas of interest in an image composed of a plurality of digital values, and more particularly to a method for displaying a visually enhanced radiograph by mapping the enhanced plurality of digital values onto a gray scale transfer (GST) function of a display medium.

BACKGROUND OF THE INVENTION

There exists significant activity in the development of digital x-ray image data capture systems. In such systems direct conversion to an electrical signal of the incident radiation is obtained using a plurality of sensors (also known as pixels) in an array. The sensor output is almost invariably immediately converted to a digital signal by an analog-to-digital converted as known in the art and further processed and stored in a databank for use in the eventual display of the data as a radiograph. U.S. Pat. No. 5,313,066 issued to Lee et al. (hereinafter the '066 patent) and U.S. Pat. No. 5,315,101 issued to Hughes et al. describe typical such sensor arrays and their contents are incorporated herein by reference. Even though several different technologies are being utilized, the output data are quite similar.

A major advantage of digital data detection systems is the wide dynamic range of signal capture. Display media, such as radiographic film or cathode ray tube (CRT) displays, on the other hand, have a substantially more limited dynamic range. A typical digital x-ray capture system can have a useful dynamic detection range of greater than a 1,000:1. However, the useful image data are generally limited to a dynamic range of less than 100:1. There is, therefore, need to determine and select the optimal limited range of useful data for diagnostic display, and then properly display such range on the available display medium.

This problem, which reduces to a need for a method whereby the exposure sensor output is mapped onto the density transfer function of the display device, has been addressed by the art in numerous ways. Typically the sensor output is digitized, and a histogram of the frequency of occurrence of digital values representing detected exposure is constructed. Following construction of the histogram, cutoff points eliminating values under selected minimum occurrence for both ends of the scale are determined and the digital values in the remaining range are mapped onto the display transfer function, usually using a look-up table (LUT), as is well known in the art. These steps are rather fundamental and intuitive. What is significant and the subject of continuing research is the manner in which the density values are processed and mapped on the transfer function to create an optimal radiograph wherein the features of interest are distinguishable from background features.

U.S. Pat. No. 5,164,993 issued Nov. 17, 1992 to Capozzi et al. together with U.S. Pat. No. 5,046,118 issued to Ajewole et al. and U.S. Pat. No. 4,868,651 issued to Chou et al., are believed to represent the current state of the art in explaining and solving the problems associated with such displays. A method for automatically identifying the range of useful digital values to be used for diagnostic display, and to provide an appropriate gray scale transfer (GST) function to optimize the diagnostic value of the final displayed image, either hard or soft copy, is described in PCT International Publication Number WO 98/37738 to Schwenker et al., and incorporated herein by reference.

Other methods are known in the art for processing matrices of digital values to provide better contrast. For example, a technique known as "unsharp masking" essentially comprises taking the original matrix of digital values, creating a "smoothed" matrix of digital values from the original matrix, and adding back the smoothed matrix to the original matrix. Creating a "smoothed" matrix entails creating a new value for each data point that is an average of a number of adjacent data points in a specified filter range. Thus, for example, a b×b smoothing filter is used where n is an odd number much less than the size of the total image matrix. The average or weighted average of each b×b matrix is used to calculate a replacement value for the central location in the b×b matrix.

The application of digital x-ray technology allows the processing of the digital image in ways that were heretofore unavailable with image acquisition directly onto film. In a typical x-ray, there may be many features of interest covering a broad range of anatomy of the patient. This broad range may include areas of anatomy having vastly disparate radiation absorption properties. As a result, an area of anatomy having relatively low radiation absorption may be relatively light on the radiograph, while an area having relatively high radiation absorption may be relatively dark. Using a typical non-digital x-ray system, multiple images at multiple radiation doses are typically created so that the features in each area can be distinguished. Some digital x-ray systems have addressed this problem using localized histogram equalization methods, simple dynamic range compression, or enhanced visualization processing.

Other methods are still desired, however, which do not compromise the contrast of the resulting image. It is thus an object of the present invention to provide a method that allows visualization of a broad range of anatomy on a single image without requiring manipulation to view light or dark areas.

SUMMARY OF THE INVENTION

The present invention comprises a method for displaying on a display medium an image corresponding to detected exposures to radiation of a plurality of sensors in an array, the detected exposures converted to a starting matrix having n rows and m columns of digital values with each digital value representing an optical density. The method comprises the steps of creating a weighted, smoothed, subtracted matrix, adding the weighted, smoothed, subtracted matrix to the starting matrix to create an enhanced matrix, and using the digital values from the enhanced matrix to display an image.

The invention also comprises a program storage device readable by machine, tangibly embodying a program of instructions executable by the machine to perform the method steps. A digital x-ray image data capture system may comprise such a program storage device as well as a source of penetrative radiation for emitting an unmodulated radiation beam along a path and a plurality of sensors in an array of n rows and m columns positioned in the beam path. The plurality of sensors is adapted for receiving and detecting exposure to at least a modulated radiation beam derived from the unmodulated radiation beam. Each sensor is adapted to produce a sensor output proportional to the detected exposure. An analog-to-digital converter adapted to receive the sensor output, convert the sensor output to a digital value, and transmit the digital value to the program storage device is also included in the system.

The digital x-ray image data capture system may be used for carrying out a method of providing a radiographic visualization of a portion of anatomy, the method comprising placing the portion of anatomy in the path of the unmodulated radiation beam between the source and the array of sensors. The unmodulated radiation beam is modulated into a modulated beam as the beam penetrates the portion of anatomy, and then the exposure of the sensors to the modulated beam is detected.

DESCRIPTION OF THE INVENTION

In a typical direct image capture set up there is a source of imaging radiation which may be x-ray radiation, a patient and a radiation detector. The patient is placed in the path of the radiation and the detector is also placed in the radiation path in a position to intercept the radiation after it has traversed the patient.

Direct radiation image capturing devices typically comprise a plurality of discrete sensors arrayed in a two dimensional array. The sensors generate and store an electrical charge that is directly proportional to the intensity and duration of the radiation incident on the sensor.

The stored charges represent the relative exposure of each sensor to the radiation. In their totality they represent a two-dimensional image of the intensity of the radiation, also known as radiation flux density, incident on the two dimensional array. The charges are next readout usually in a prescribed sequence. Readout of the stored charges produces electrical signals representing the sensor's exposure. Following amplification and noise filtering the electrical signals which typically are analog signals at this point, are almost always converted to digital values representing the relative exposure of each sensor. The digital values are stored in a data storage medium referred to herein as a data bank. Storage is in a manner that permits the accurate two-dimensional reconstruction of the charge distribution initially stored on the array. This original set of digital values is referred to hereinafter as MATRIX_0.

Figure 1:
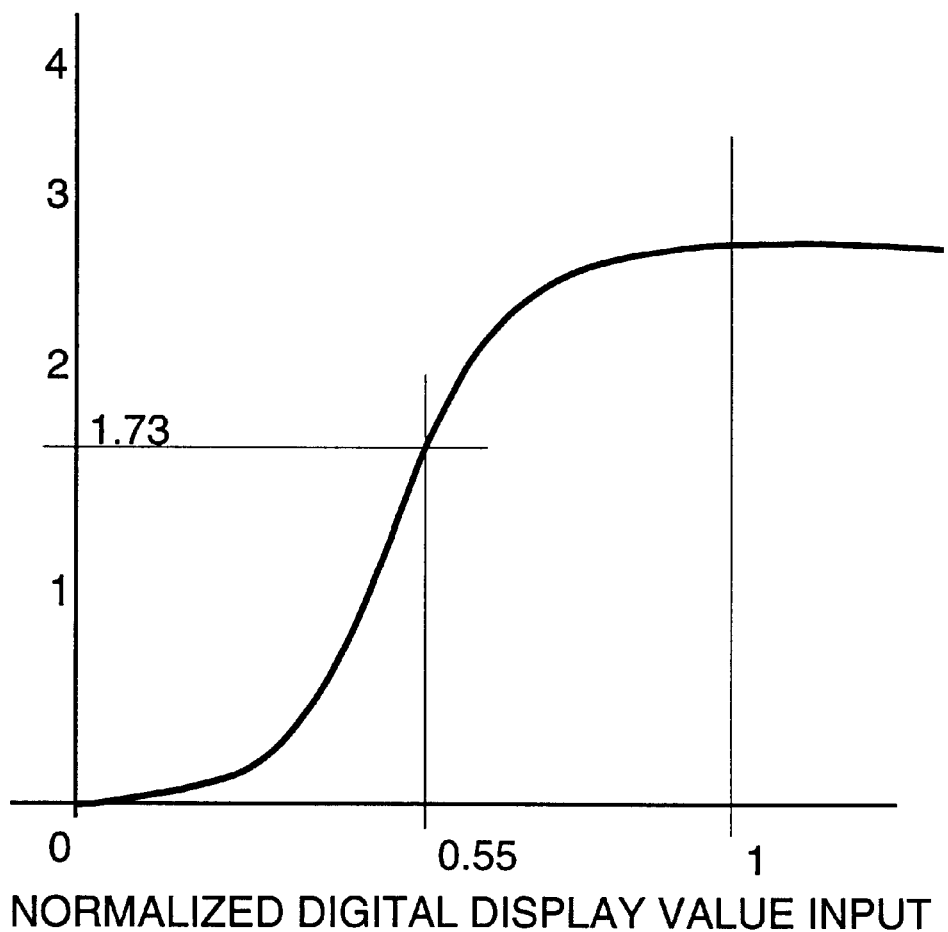
FIG. 1 is a graphic representation showing a typical gray scale transfer function for a display medium giving the resulting optical density as a function of input digital values.

In displaying an image, digital values are used as an input to a display apparatus to produce a gray scale representation on a display screen or to expose a photosensitive film. FIG. 1 graphically depicts a typical gray scale transfer (GST) function 10 that illustrates on the y-axis the corresponding optical density in the display for each digital value on the x-axis input to the apparatus. In this example the display medium is a photosensitive film having a maximum density of about 3.0. Although shown graphically in FIG. 1 for illustrative purposes, GST function 10 is typically represented in the form of a look-up table in a computer memory.

The information in the data bank is used for displaying a visual image of the charge distribution in the form of a two dimensional distribution of digital values each value corresponding to the accumulated charge by each of the sensors in the array. These charges form the picture elements or pixels that constitute the displayed image.

The digital values stored in the data bank are raw values in the sense that they are a numerical representation of the magnitude of the charge generated and stored in the radiation detectors as a result of their exposure to radiation. This charge magnitude as a function of exposure is most often a linear relationship that extends over a wide dynamic range. A direct representation of the stored information on the display, whether it is film or CRT typically results in a lot of information getting lost due to the desire to depict portions of the image data at a desired contrast and density level.

A histogram of the digital values representing the incident x-ray flux density on the detector will give an indication of the range of useful image data values to be utilized for generating the display image. To limit the size of the blocks of data being handled, it is preferred that the histogram be a "reduced histogram" constructed using logarithmic data values and still more preferably by placing the data in "bins" of a number of discrete data values, as is described in more detail herein later.

A typical such histogram and exemplary methods for deriving various reference values are described in International Publication Number WO 98/37738, incorporated herein by reference and referred to hereinafter as "the '738 Publication":

DVlow—a percentage (for example, 5%) of the integral of the histogram

DVpeak—a first point from right to left on the integral where the slope of the integral first changes direction, or the highest peak in the histogram to the left of DVedge DVedge—the point where the histogram population drops to less than a preselected percentage (for example, 75%) of the highest preceding peak as the histogram is scanned from left to right.

DVmin & DVmax—the low and high points, respectively, of the range of digital values used in displaying the captured image, calculated from DVlow, DVpeak and DVedge based using exam-specific algorithms Although the method described in the '738 Publication is preferable, the above values, or analogous values thereto, may be derived by any methods or algorithms known in the art. Other techniques may be applied prior to developing the final histogram, including the use of blocking filters or other methods as described in co-pending U.S. application Ser. No. 09/196,391 to Cornell Williams, hereinafter "the '391 Application." The purpose of such processing is to identify the "useful range" of the data values (the values between and including DVmin and DVmax) that provides meaningful diagnostic information to the user. Thus, any method for determining the useful range of data within the matrix may be employed.

As described in the '738 Publication, in a typical radiographic system the dynamic range of the radiation exposure—the radiation levels multiplied by the duration of the exposure—may be from 10×10E-6 roentgens to 100,000×10E-6 roentgens, or 10,000 to 1. For better manageability, this dynamic range may be reduced prior to the histogram construction by using logarithmic conversion and digitization into a 12-bit system having 4096 log values. In the preferred mode for constructing the histogram as described in the '738 Publication, rather than using the individual digital exposure values, bins having a certain number of sequential values in the bin are used. For instance, each bin may include 20 sequential digital values. Thus, in a case where the digital system is a 12-bit system, there are 4096 discreet values, which may be reduced to 205 by dividing the range into bins of 20 sequential values and tracking the frequency of occurrence of any value within a bin as the frequency of occurrence for that bin. Thus, the "reduced" histogram may comprise 205 "binned" values each representing the frequency of occurrence of 12-bit logarithmic values in that bin. As used herein, the prefix "DV" indicates that a value is a 12-bit, binned, logarithmic value in accordance with a preferred embodiment of this invention. The histogram may be reduced in any number of ways, or may be left unreduced if desired, and thus the illustration of the principles of this invention with reference to reduced values is not intended as a limitation on the broad invention as claimed herein.

Figure 2:
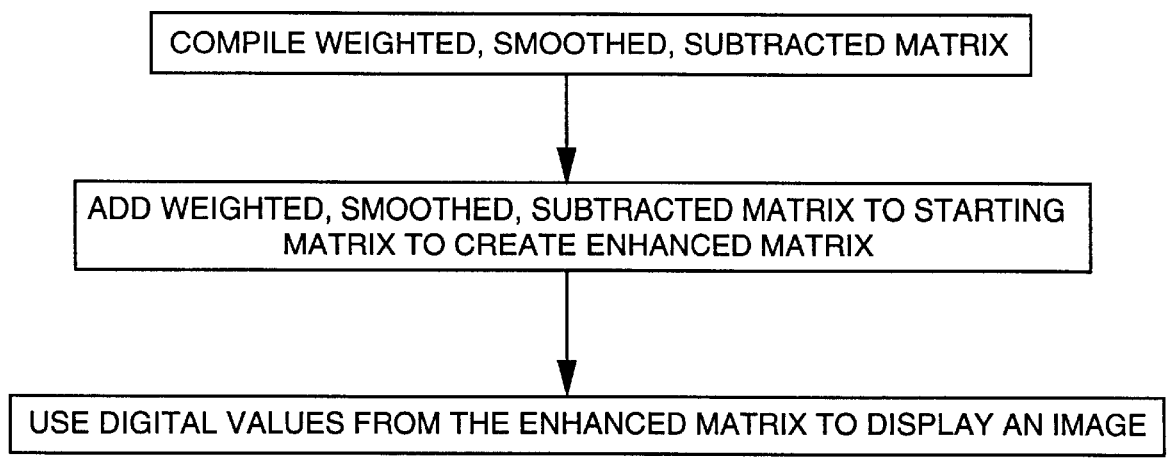
FIG. 2 is a flow diagram depicting an exemplary set of general steps according to a broad embodiment of this invention.
Figure 3:
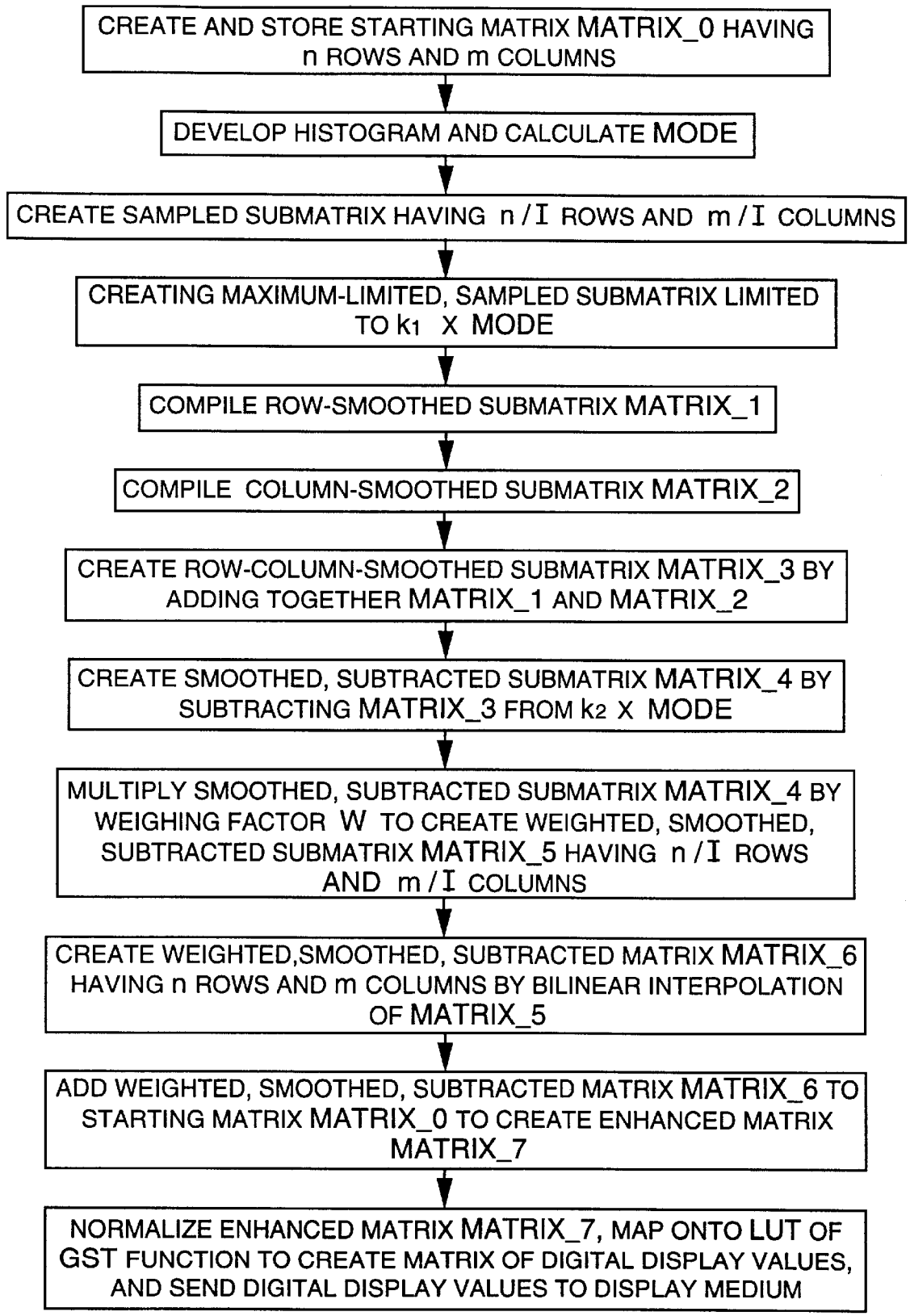
FIG. 3 is a flow diagram depicting an exemplary set of detailed steps according to a specific embodiment of this invention.

Referring now to FIGS. 2 and 3, there are shown a flowchart depicting a very general embodiment of the invention and a flowchart depicting a detailed embodiment of the invention, respectively. The flowcharts are self-explanatory and serve as a quick summary for the description that follows. The method according to this invention preferably employs a histogram, such as the histogram described above. The starting histogram for this invention, however, may be any histogram of digital values corresponding to the radiation exposure of an array of pixels in a digital x-ray receiver. According to one embodiment of the present invention, first, an anchor point (ANCHOR), preferably the mode of the histogram (the digital value having the highest frequency of occurrence—hereinafter, "DVmode"), is determined. It may be beneficial to limit the range of values from which the mode may be selected, to only the values between some predetermined minimum and maximum histogram value. For example, the range can be limited to only those values between DVlow and the quantity equal to DVlow plus 80% of the difference between DVhigh and DVlow. It also may be beneficial to first smooth the histogram before determining the mode. Thus, for example, the reduced histogram as derived consistent with the method described in the '738 Publication and summarized above, containing 205 values denoting a frequency of occurrence in each bin, may be further smoothed with a 15-bin filter such that the bin frequency of occurrence is averaged over a 15 bin range. Once the DVmode is determined from a histogram of 12-bit, logarithmic, binned values as described above, however, the value is then converted back to a 14-bit value for the mode. Procedures for conversion of values from 12-bit to 14-bit and vice versa are well-known in the art, and are discussed in detail in the '738 Publication.

The numerical range of data used in the histogram can also be modified based on techniques described in the '391 Application, making selection of the mode more customized to the particular image type. For example, for a chest x-ray, only those portions of the x-ray image representing the lung may be important in assessing the mode and thus other areas can be excluded from the histogram.

Although the mode is a preferred value for the anchor point, the anchor point may be any value desired to be the focal point about which the data is processed. The anchor point may be representative of a particular density desired on the display, or preferably any point that is a representative point for the majority of meaningful data gathered in the digital radiograph. Thus, although creating the histogram is desirable in a preferred embodiment of the invention, the invention may be practiced without creating such a histogram. Where the reduced histogram has been derived, another potential value for the anchor point may be the 14-bit value corresponding to 35% times the midpoint between DVmax and DVmin, plus DVmin. Such a value tends to be greater than the mode, but may be used as a "safety point" such that the anchor point can be chosen to be the lower of the mode or the safety point, in case the calculation of the mode results in a value so high that it would result in visually poor results.

Once an anchor point has been determined, typically a sampled, representative set of values is created from MATRIX_0. MATRIX_0 typically comprises a matrix of digital values (n,m) corresponding to the n rows and m columns of discrete sensors in the digital x-ray panel. Thus, for example, a typical array comprising 3072 rows and 2560 columns of sensors results in MATRIX_0 having over 7.8 million values. Creating the sampled set of values makes the matrix more manageable for processing. The sampled set of values preferably takes the form of a submatrix (n/I, m/I') where I and I' are integers, preferably equal to one another, and n/I and m/I' are also integers. For example, it may be desirable to compile a matrix using only every $16^{th}$ value in each row and column in the 3070×2560 matrix, creating a new matrix of values that is 192×160 (30,720 values). If n/I and m/I are not integers, then the values can be truncated to integers trunc(n/I) and trunc(m/I), respectively, such that the matrix has the dimensions (trunc(n/I), trunc(m/I)). Although the sampling step is important as a practical matter to be able to process the numerical data with minimal computational requirements, the starting matrix may be manipulated in accordance with the remaining steps of this invention without first creating the sampled matrix.

To eliminate potential edge effects due to artifacts associated with the positioning of radiation sensors near the edge of the matrix, several rows and columns of data on the edges of the matrix may be set to the corresponding value in an expectedly reliable row or column. Thus, for instance, the value for the data point in the first three rows of every column in the sampled matrix may be set to the value of the data point in the fourth row of that column. Similarly, the value for the data point in the first three columns of every row in the sampled matrix may be set to the value of the data point in the fourth column of that row.

The sampled matrix, also referred to herein as a "sampled submatrix", is then processed. In a first step, the values in the submatrix may be limited to a maximum value (SUBMAX), preferably equal to a constant times the anchor point (i.e. SUBMAX=$k_1$×ANCHOR). If no anchor point has been derived, however, the maximum value may be chosen by some other criteria, such as a standard maximum for a specific type of exam. Thus, if the digital value in the submatrix is greater than SUBMAX, it is replaced by SUBMAX. The resulting submatrix may be referred to as a "maximum-limited sampled submatrix." Constant $k_1$ is based on the image content and may be derived empirically or automatically calculated.

Next, the submatrix is smoothed along the rows to create a row-smoothed submatrix MATRIX_1) and smoothed along the columns to create a column-smoothed submatrix MATRIX_2). Preferably, the submatrix is linearly smoothed. Linear smoothing entails replacing the central value of an odd-numbered group of linearly adjacent values with the average or weighted average of the group of values. Thus, for example, a 19-point smoothing filter calculates an average from the group of values including the data point in the center and the 9 points on either side of the center point. The value for the center point is then replaced by the calculated average. To smooth points near the edge of an array (for example, the ninth point or less from the edge when using a 19-point filter), the number of points in the filter is reduced, or the edge points are not smoothed at all. For example, the $9^{th}$ point in can be smoothed by a 17-point filter, the $8^{th}$ point by a 15-point filter, and so on, or a 3-point filter can be chosen for all points between the second and ninth points.

The smoothing may preferably occur along an individual line (row or column) such that the physical distance over which the data are smoothed is on the order of 4 to 5 cm of the actual anatomical data (and corresponding anatomy). For example, for an image sampled by a factor of 16 and smoothed by a factor of 19, where the pixel data represent a 0.139 mm×0.139 mm actual size in the digital detector, the smoothing distance is 16×19×0.139 mm=42.256 mm (4.2 cm) along the digital detector.

The smoothed submatrices are then added together to create a row-column-smoothed submatrix (i.e. MATRIX_3=MATRIX_1+MATRIX_2). The row-column-smoothed submatrix comprises only selected points of the full matrix, but is capable of communicating useful information about the relative density in each portion of the matrix in the vicinity of each submatrix point, much in the same way that a topographical map is useful for illustrating relative elevations across an entire map using discrete lines representing predetermined elevation intervals. Accordingly, the row-column-smoothed submatrix has also been referred to by the inventors as a "topographical matrix". Although one method of deriving the topographical matrix or smoothed submatrix is disclosed herein, similar submatrices derived via other methods of sampling and processing, can also be used for the further steps in the method of this invention.

Next, a fourth submatrix (MATRIX_4) is created by subtracting each value in MATRIX_3 from a fixed value greater than each value in MATRIX_3. In a preferred embodiment, the fixed value is equal to a constant $k_2$ times the value of the anchor point (i.e. MATRIX_4=$k_2$× ANCHOR−MATRIX_3). This creates a "smoothed, subtracted submatrix" or "inverse topographical matrix." As used herein, "inverse" or "subtracted" as applied to a matrix denotes that the matrix has been subtracted from a larger, fixed value, so that the formerly relatively light areas in the corresponding image become relatively dark, and the formerly relatively dark areas in the corresponding image become relatively light.

Next, a fifth submatrix MATRiX_5 is created by multiplying each value in MATRIX_4 by a weighing factor w (i.e. MATRIX_5=w×MATRIX_4) where w is a value less than 1. Thus, the resulting submatrix MATRIX_5 can be described as a "weighted, smoothed, subtracted submatrix" or a "weighted, inverse topographical matrix, hence the "weighted inverse topography method" provided as the title to this invention. Next, the n/I×m/I submatrix of values in MATRIX_5 is extrapolated into an n×m matrix of values (MARTIX_6), preferably using bilinear interpolation to fill in the values not present in MATRIX_5. The resulting matrix MATRIX_6 can be described as a weighted, smoothed, subtracted matrix, as opposed to a submatrix. MATRIX_6 is then added to MATRIX_0 to create MATRIX_7 (i.e. MATRIX_7=MATRIX_0+MATRIX_6). "Weighted" as used above denotes that the values in the sampled and expanded matrices are scaled relative to the original matrix of values, such that the impact of adding the weighted, smoothed, subtracted matrix to the original matrix will only modify the original matrix by a certain percentage. A heavier weighing factor will produce a more profound effect than a lighter weighing factor. It should be noted that the weighing factor may be applied at any time prior to creating the enhanced matrix, including after the extrapolation of a smoothed, subtracted submatrix into a smoothed, subtracted matrix, or even before the smoothing steps. The weighing factor and fixed value used for creating the subtracted matrix thus may be coordinated to produce the desired result.

MATRIX_7 is next normalized, as is well-known in the art, by converting each value in the matrix to a decimal representing the percentage of the maximum value in the matrix, with the maximum value set to 1. Thus, the resulting normalized range of values in the matrix is between 0 and 1. This normalized set of values is applied to a look-up table (LUT) representing the gray scale transfer (GST) function for the particular medium on which the image is to be displayed, as shown in FIG. 1, and thus is converted to a new set of digital values, referred to as the mapped display data. The mapped display digital values are next sent to the apparatus used for generating the display.

The dynamic range of the digital values in the sampled submatrix prior to creating MATRIX_1 and MATRIX_2 and in the enhanced matrix MATRIX_7 may be reduced in the upper and/or lower portions of the dynamic range. The upper portion of the range may be defined, for example, as data values exceeding 4×ANCHOR. The dynamic range in the upper portion of the range may be reduced by applying a scaling factor, such as for example, multiplying each upper portion data value by a factor such as DVmaxm14/DVmax14 wherein DVmax14 is the 14-bit, non-log, non-bin equivalent of DVmax and DVmaxm14 is, for example, the 14-bit, non-log, non-bin equivalent of the lesser of: (a) 5×DVmode, or (b) 0.7×DVmax. Other scaling factors may be used, however, as desired. Typically, the dynamic range in the lower portion is sufficiently reduced just using the weighting of the weighted, smoothed, subtracted matrix as described above, but other adjustments using scaling factors may also be applied. If such adjustment is performed, although the desired lower portion of the range to be adjusted may comprise only the values lower than the 14-bit, non-log, non-bin equivalent of DVmin, values up to the anchor point may need to be adjusted to create the desired visual effect. Also, DVmin can also be selected in the histogram processing portion of the method to create a desired low-range effect.

A plurality of GST functions are preferably stored as LUTs, each function representing a different response, similar to using different contrast and speed film in traditional radiography. Thus, a plurality of different displays may be provided for the same data, permitting the display to be tailored to a particular individual's taste based on the GST function selected for use, providing extra flexibility.

Constants $k_1$ and $k_2$ and weighing factor w are referenced throughout this description. These constants and factor may be determined empirically by first entering a value in the equation and observing a displayed image. A decision as to what constitutes an image of good diagnostic quality is a highly personal one and the selection of constants that will produce the best image for all people in all instances is not a realistic undertaking. Through experimentation and experience, constant values of $k_1=5$ and $k_2=2$ have been found to be preferred where the anchor point used is the 14-bit, non-log, non-bin equivalent of the mode of the reduced histogram, but by no means should these be considered limiting values. The weighing factor w tends to be more anatomy-specific. Preferred, but by no means limiting, ranges preferred by the inventors are provided in Table 1 below. These given constants are intended merely to provide guidance for users of the present invention. If the resulting displays are not to the user's subjective satisfaction, the values can serve as a good starting point towards the development of other values that may produce subjectively better results.

TABLE 1

| ANATOMY | PREFERRED RANGE FOR w |
|---|---|
| Upper Extremities | 0.1–0.15 |
| Lower Extremities | 0.15–0.25 |
| Skull, Pelvis, Shoulder, Abdomen, Hips, Spine | 0.3–0.4 |
| Chest/Lung | 0.2–0.3 |

In carrying out the present method, it is important to establish proper limits for constants $k_1$ and $k_2$ and weighing factor w so that image artifacts are not introduced around high-density structures (such as lead markers) within the image. Similarly, proper selection of constant $k_1$ and $k_2$ and weighing factor w also prevents over-enhancement of the image. Other parameters within the image acquisition and processing system may also need to be optimized to provide optimum results, such optimization being application-specific and requiring adjustment by trial and error as warranted. Once the method of the present invention has been performed on a matrix of digital values, it is not easily reversed, and thus the starting matrix should remain stored in the event the method must be performed again with a different constant or a different weighing factor.

The method of the present invention enables the visualization of a broad range of contrast-enhanced anatomy in a single display image. The enhanced contrast of the images may be useful in any number of applications, including but not limited to, general radiography and mammography. The present method provides this enhanced visualization without increasing noise, and provides some scatter correction. Because the method applies an inverse topographical correction to the data matrix, the method provides enhanced contrast rather than a mere density shift, thus providing additional diagnostic information as compared to prior methods of data correction. The method also normalizes variations in x-ray intensity across the field of view. The method eliminates the need for localized histogram equalization methods or simple dynamic range compression.

Figure 4:
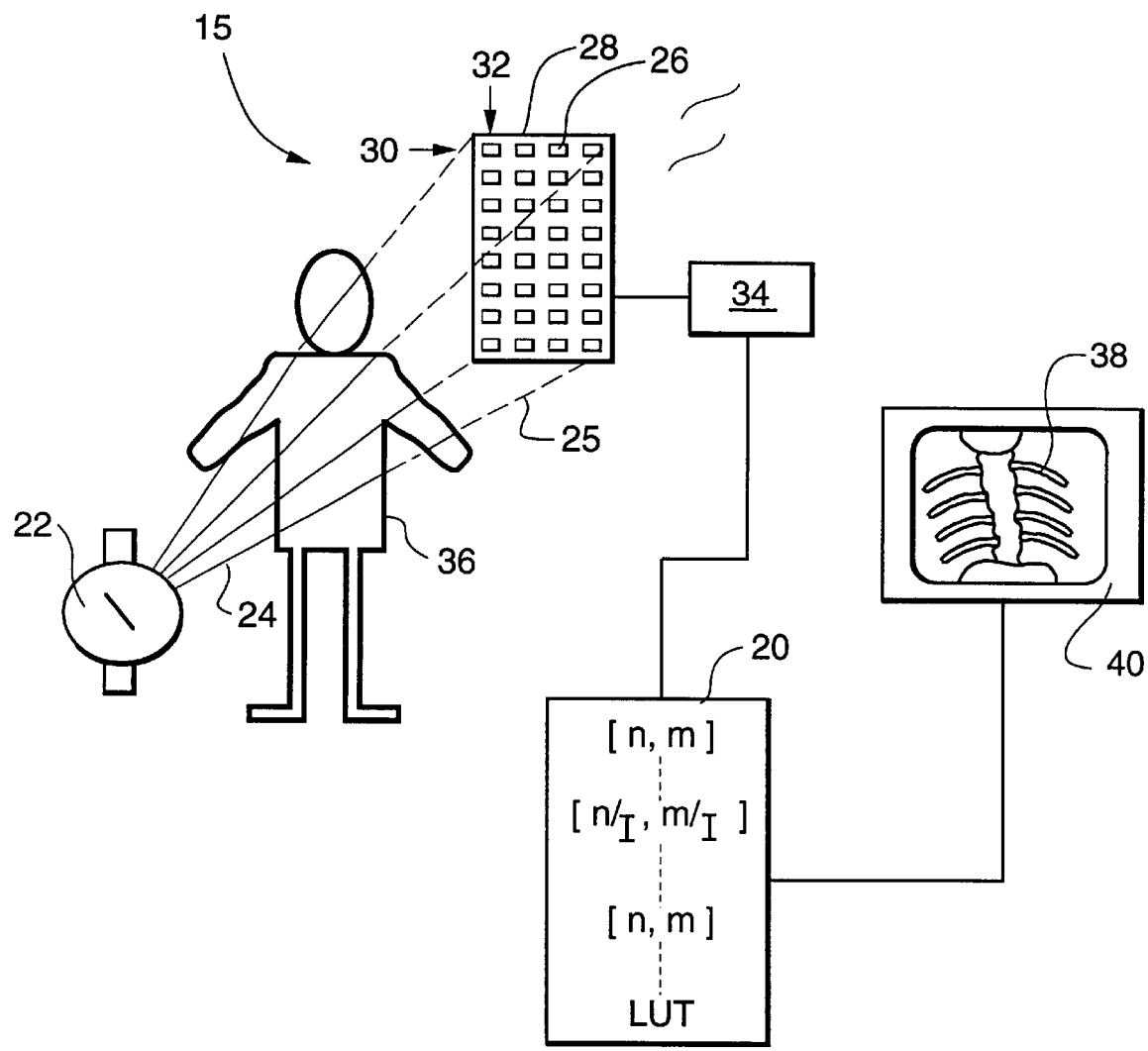
FIG. 4 is a schematic diagram depicting an exemplary embodiment of a digital x-ray image data capture system according to this invention in use according to a method of the invention.

It is obvious that while the conversions and calculations may be done in hardware with operator input at various stages, the computational portion of this process is best be done using a computer or other program storage device appropriately programmed. Referring now to FIG. 4, such a program storage device 20 may thus be part of a digital x-ray image data capture system 15 further comprising a source 22 of penetrative radiation for emitting an unmodulated radiation beam 24 along a path, and a plurality of sensors 26 in an array 28 of n rows and m columns positioned in the path of beam 24 for receiving and detecting radiation exposure. Each sensor is adapted to produce a sensor output, typically an analog output, proportional to the detected exposure. An analog-to-digital (A/D) converter 34 adapted to receive the sensor output is thus also provided to convert the sensor output to a digital value and transmit the digital value to program storage device 20. The radiation exposure detected by the sensors is typically a modulated radiation beam 25 derived from the modulation of unmodulated radiation beam 24 passing through a portion of anatomy 36 desired for radiographic visualization.

Thus, digital x-ray image data capture system 15 described above may be used in a method for radiographically visualizing of portion of anatomy 36 placed in the path of unmodulated radiation beam 24 between source 22 and array 28 of sensors 26. Unmodulated radiation beam 24 is modulated into modulated beam 25 as the beam penetrates portion of anatomy 36, and then the exposure of sensors 26 to the modulated beam is detected. The detected exposures are then processed in program storage means 20 by the methods detailed above, and the resulting image 38 is displayed on display medium 40, shown in FIG. 4 as a CRT.

Figure 7:
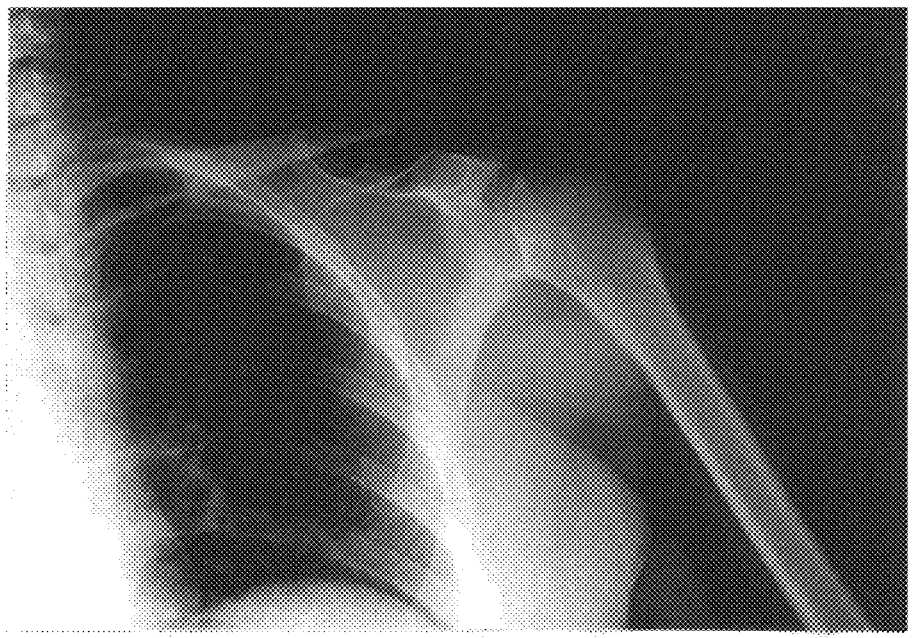
FIG. 7 is an exemplary radiograph produced from a starting matrix of digital values prior to processing by the method of this invention.
Figure 8:
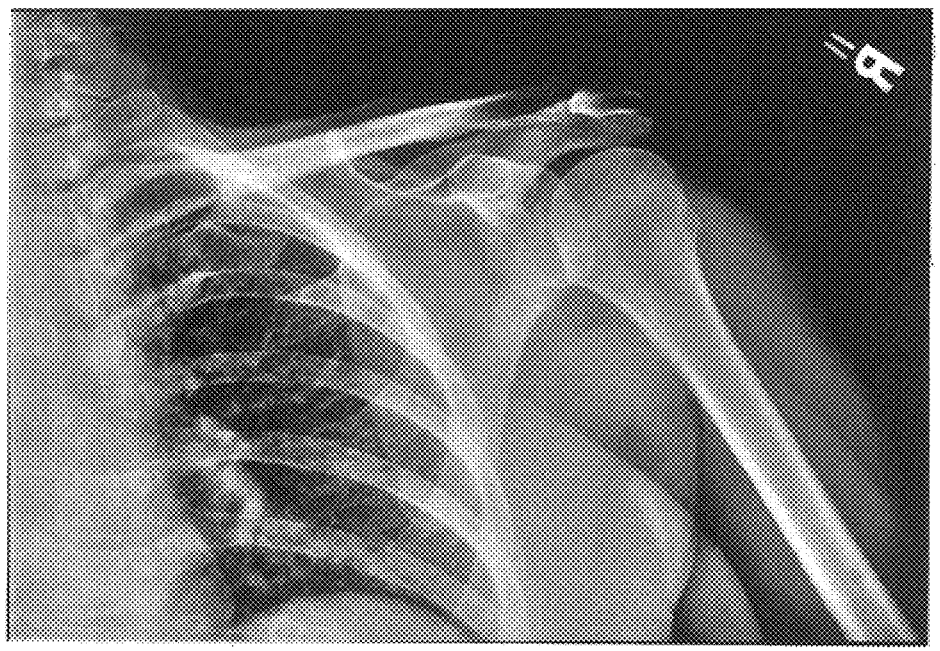
FIG. 8 is an exemplary radiograph derived from the matrix of digital values corresponding to FIG. 7 after the values have been processing by an exemplary method of this invention.

Referring now to FIGS. 7 and 8, there is shown a portion of an image derived from actual radiographic data (not shown) before (FIG. 7) and after (FIG. 8) processing of the data by an exemplary method of this invention.

EXAMPLE

Figure 5:
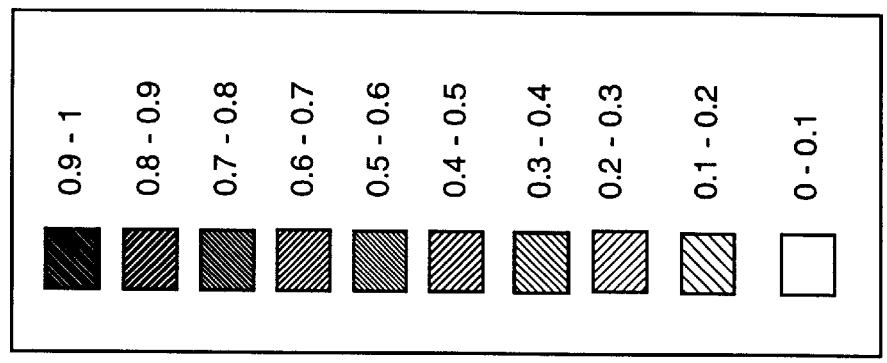
FIG. 5 is a normalized, 3-dimensional plot of the data provided in starting matrix MATRIX_0 of the example.
Figure 5:
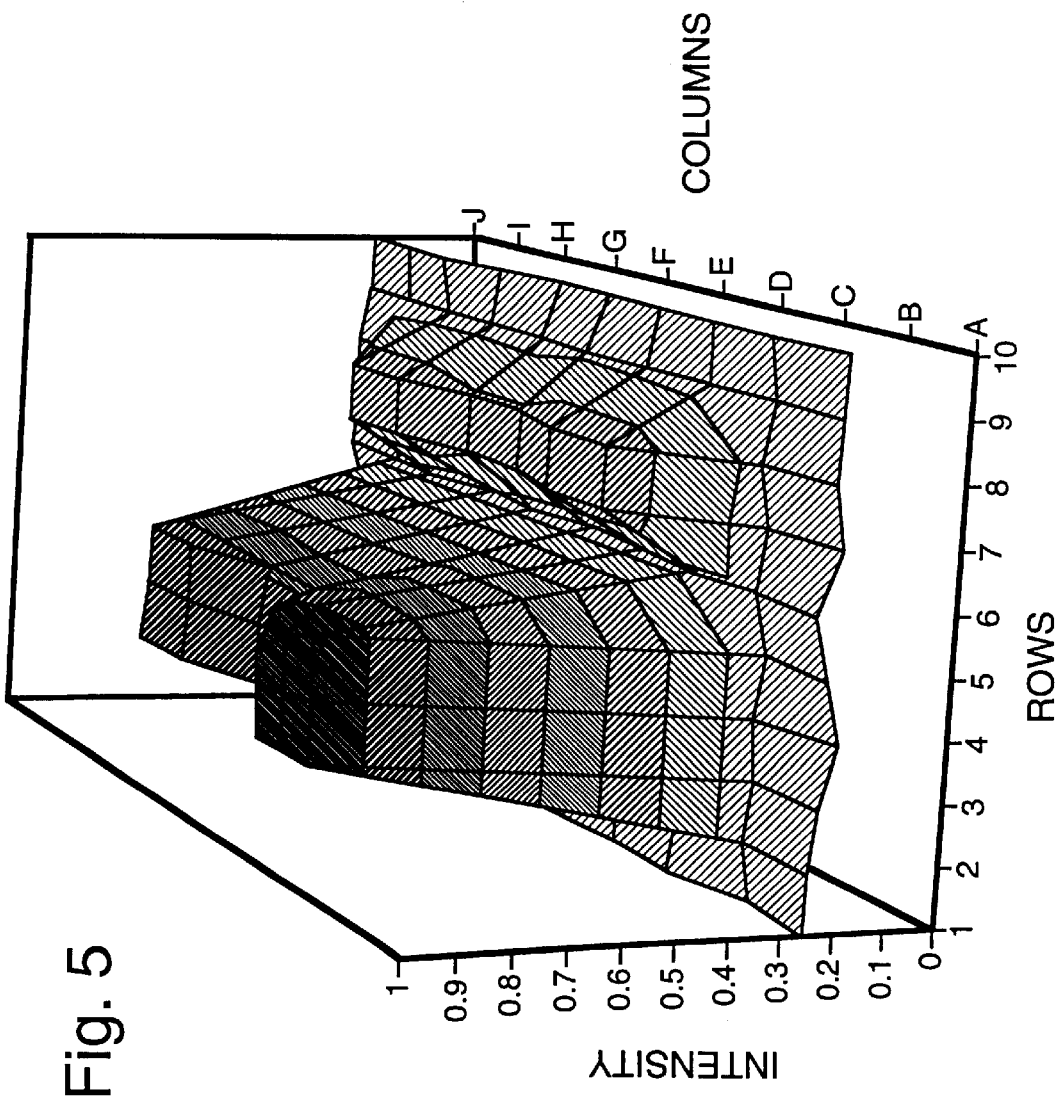

The following example is included to more clearly demonstrate the overall nature of the invention. This example is exemplary, not restrictive, of the invention. Although the vast quantity of data necessary to produce a meaningful radiograph cannot be reasonably shown herein, a 10×10 matrix below (MATRIX_0) is provided to show how the exemplary steps are carried out on a set of values. These values have been arbitrarily chosen between 0 and 100, and are not intended to bear any relation to the raw values generally produced by digital x-ray sensors. A normalized 3-dimensional plot of MATRIX_0 is shown in FIG. 5. As shown in FIG. 5, the matrix of values has been generated to produce features visible on the 3-D plot at two different levels of intensity relative to the background noise.

|  | A | B | C | D | E | F | G | H | I | J |
|---|---|---|---|---|---|---|---|---|---|---|
| ROW 1 | 25 | 23 | 27 | 26 | 27 | 26 | 25 | 26 | 25 | 22 |
| ROW 2 | 25 | 25 | 26 | 27 | 28 | 26 | 26 | 25 | 24 | 23 |
| ROW 3 | 24 | 24 | 97 | 97 | 79 | 79 | 86 | 86 | 25 | 24 |
| ROW 4 | 21 | 25 | 98 | 98 | 80 | 80 | 85 | 85 | 21 | 25 |
| ROW 5 | 24 | 23 | 96 | 96 | 78 | 78 | 85 | 85 | 25 | 21 |
| ROW 6 | 27 | 26 | 27 | 25 | 24 | 25 | 23 | 26 | 24 | 25 |
| ROW 7 | 23 | 25 | 45 | 45 | 40 | 40 | 45 | 45 | 25 | 25 |
| ROW 8 | 25 | 27 | 45 | 45 | 40 | 40 | 45 | 45 | 26 | 25 |
| ROW 9 | 25 | 25 | 26 | 27 | 28 | 26 | 26 | 25 | 24 | 23 |
| ROW 10 | 25 | 27 | 26 | 25 | 24 | 23 | 25 | 27 | 25 | 23 |

MATRIX_0

As MATRIX_0 was already small enough to be readily manageable, no sampling was necessary. Furthermore, because the values were arbitrarily chosen to be within desired limits, no maximum limiting was necessary. Thus, MATRIX_0 was next row-smoothed to create MATRIX_1 using no smoothing on columns A and J, a 3-point filter on columns B and I, and a 5-point filter on columns C through H. MATRIX_0 was also column-smoothed to create MATRIX_2 using no smoothing on rows 1 and 10, a 3-point filter on rows 2 and 9, and a 5-point filter on rows 3 through 8. The following matrices MATRIX_1 and MATRIX_2 thus resulted:

MATRIX_1

|        | A   | B    | C    | D    | E    | F    | G    | H    | I    | J    |
|--------|-----|------|------|------|------|------|------|------|------|------|
| ROW 1  | 25  | 25   | 25.6 | 25.8 | 26.2 | 26   | 25.8 | 24.8 | 24.3 | 22   |
| ROW 2  | 25  | 25.3 | 26.2 | 26.4 | 26.6 | 26.4 | 25.8 | 24.8 | 24   | 23   |
| ROW 3  | 24  | 48.3 | 64.2 | 75.2 | 87.6 | 85.4 | 71   | 60   | 45   | 24   |
| ROW 4  | 21  | 48   | 64.4 | 76.2 | 88.2 | 85.6 | 70.2 | 59.2 | 43.7 | 25   |
| ROW 5  | 24  | 47.7 | 63.4 | 74.2 | 86.6 | 84.4 | 70.2 | 58.8 | 43.7 | 21   |
| ROW 6  | 27  | 26.7 | 25.8 | 25.4 | 24.8 | 24.6 | 24.4 | 24.6 | 25   | 25   |
| ROW 7  | 23  | 31   | 35.6 | 39   | 43   | 43   | 39   | 36   | 31.7 | 25   |
| ROW 8  | 25  | 32.3 | 36.4 | 39.4 | 43   | 43   | 39.2 | 36.2 | 32   | 25   |
| ROW 9  | 25  | 25.3 | 26.2 | 26.4 | 26.6 | 26.4 | 25.8 | 24.8 | 24   | 23   |
| ROW 10 | 25  | 26   | 25.4 | 25   | 24.6 | 24.8 | 24.8 | 24.6 | 25   | 23   |

MATRIX_2

|        | A    | B    | C    | D    | E    | F    | G    | H    | I    | J    |
|--------|------|------|------|------|------|------|------|------|------|------|
| ROW 1  | 25.0 | 23.0 | 27.0 | 26.0 | 27.0 | 26.0 | 25.0 | 26.0 | 25.0 | 22.0 |
| ROW 2  | 24.7 | 24.0 | 50.0 | 50.0 | 44.7 | 43.7 | 45.7 | 45.7 | 24.7 | 23.0 |
| ROW 3  | 23.8 | 24.0 | 68.8 | 68.8 | 58.4 | 57.8 | 61.4 | 61.4 | 24.0 | 23.0 |
| ROW 4  | 24.2 | 24.6 | 68.8 | 68.6 | 57.8 | 57.6 | 61.0 | 61.4 | 23.8 | 23.6 |
| ROW 5  | 23.8 | 24.6 | 72.6 | 72.2 | 60.2 | 60.4 | 64.8 | 65.4 | 24.0 | 24.0 |
| ROW 6  | 24.0 | 25.2 | 62.2 | 61.8 | 52.4 | 52.6 | 56.6 | 57.2 | 24.2 | 24.2 |
| ROW 7  | 24.8 | 25.2 | 47.8 | 47.6 | 42.0 | 41.8 | 44.8 | 45.2 | 24.8 | 23.8 |
| ROW 8  | 25.0 | 26.0 | 33.8 | 33.4 | 31.2 | 30.8 | 32.8 | 33.6 | 24.8 | 24.2 |
| ROW 9  | 25.0 | 26.3 | 32.3 | 32.3 | 30.7 | 29.7 | 32.0 | 32.3 | 25.0 | 23.7 |
| ROW 10 | 25.0 | 27.0 | 26.0 | 25.0 | 24.0 | 23.0 | 25.0 | 27.0 | 25.0 | 23.0 |

MATRIX_1 and MATRIX_2 were then added together to produce MATRIX_3:

MATRIX_3

|        | A    | B    | C     | D     | E     | F     | G     | H     | I    | J    |
|--------|------|------|-------|-------|-------|-------|-------|-------|------|------|
| ROW 1  | 50.0 | 48.0 | 52.6  | 51.8  | 53.2  | 52.0  | 50.8  | 50.8  | 49.3 | 44.0 |
| ROW 2  | 49.7 | 49.3 | 76.2  | 76.4  | 71.3  | 70.1  | 71.5  | 70.5  | 48.7 | 46.0 |
| ROW 3  | 47.8 | 72.3 | 133.0 | 144.0 | 146.0 | 143.2 | 132.4 | 121.4 | 69.0 | 47.0 |
| ROW 4  | 45.2 | 72.6 | 133.2 | 144.8 | 146.0 | 143.2 | 131.2 | 120.6 | 67.5 | 48.6 |
| ROW 5  | 47.8 | 72.3 | 136.0 | 146.4 | 146.8 | 144.8 | 135.0 | 124.2 | 67.7 | 45.0 |
| ROW 6  | 51.0 | 51.9 | 88.0  | 87.2  | 77.2  | 77.2  | 81.0  | 81.8  | 49.2 | 49.2 |
| ROW 7  | 47.8 | 56.2 | 83.4  | 86.6  | 85.0  | 84.8  | 83.8  | 81.2  | 56.5 | 48.8 |
| ROW 8  | 50.0 | 58.3 | 70.2  | 72.8  | 74.2  | 73.8  | 72.0  | 69.8  | 56.8 | 49.2 |
| ROW 9  | 50.0 | 51.7 | 58.5  | 58.7  | 57.3  | 56.1  | 57.8  | 57.1  | 49.0 | 46.7 |
| ROW 10 | 50.0 | 53.0 | 51.4  | 50.0  | 48.6  | 47.8  | 49.8  | 51.6  | 50.0 | 46.0 |

Using MODE=50, $k_2$=2, and weighting factor w=0.3, each value in the smoothed MATRIX_3 was subtracted from $k_2 \times$MODE to create MATRIX_4 (not shown) and then MATRIX_4 multiplied by w. Therefore the values in weighted, smoothed, subtracted matrix MATRIX_5 correspond to $w \times (k_2 \times \text{MODE} - \text{MATRIX\_3})$:

MATRIX_5

|       | A    | B    | C     | D     | E     | F     | G     | H    | I    | J    |
|-------|------|------|-------|-------|-------|-------|-------|------|------|------|
| ROW 1 | 15.0 | 15.6 | 14.2  | 14.5  | 14.0  | 14.4  | 14.8  | 14.8 | 15.2 | 16.8 |
| ROW 2 | 15.1 | 15.2 | 7.1   | 7.1   | 8.6   | 9.0   | 8.6   | 8.9  | 15.4 | 16.2 |
| ROW 3 | 15.7 | 8.3  | -9.9  | -13.2 | -13.8 | -13.0 | -9.7  | -6.4 | 9.3  | 15.9 |
| ROW 4 | 16.4 | 8.2  | -10.0 | -13.4 | -13.8 | -13.0 | -9.4  | -6.2 | 9.8  | 15.4 |
| ROW 5 | 15.7 | 8.3  | -10.8 | -13.9 | -14.0 | -13.4 | -10.5 | -7.3 | 9.7  | 16.5 |
| ROW 6 | 14.7 | 14.4 | 3.6   | 3.8   | 6.8   | 6.8   | 5.7   | 5.5  | 15.2 | 15.2 |
| ROW 7 | 15.7 | 13.1 | 5.0   | 4.0   | 4.5   | 4.6   | 4.9   | 5.6  | 13.1 | 15.4 |

-continued

|        | A    | B    | C    | D    | E    | F    | G    | H    | I    | J    |
|--------|------|------|------|------|------|------|------|------|------|------|
| ROW 8  | 15.0 | 12.5 | 8.9  | 8.2  | 7.7  | 7.9  | 8.4  | 9.1  | 13.0 | 15.2 |
| ROW 9  | 15.0 | 14.5 | 12.4 | 12.4 | 12.8 | 13.2 | 12.7 | 12.9 | 15.3 | 16.0 |
| ROW 10 | 15.0 | 14.1 | 14.6 | 15.0 | 15.4 | 15.7 | 15.1 | 14.5 | 15.0 | 16.2 |

As MATRIX_5 is not a sampled submatrix, no extrapolation to create a MATRIX_6 was necessary. Therefore, next, enhanced MATRIX_7 was created by adding MATRIX_0 and MATRIX_5:

MATRIX_7

|        | A    | B    | C    | D    | E    | F    | G    | H    | I    | J    |
|--------|------|------|------|------|------|------|------|------|------|------|
| ROW 1  | 40.0 | 38.6 | 41.2 | 40.5 | 41.0 | 40.4 | 39.8 | 40.8 | 40.2 | 38.8 |
| ROW 2  | 40.1 | 40.2 | 33.1 | 34.1 | 36.6 | 35.0 | 34.6 | 33.9 | 39.4 | 39.2 |
| ROW 3  | 39.7 | 32.3 | 87.1 | 83.8 | 65.2 | 66.0 | 76.3 | 79.6 | 34.3 | 39.9 |
| ROW 4  | 37.4 | 33.2 | 88.0 | 84.6 | 66.2 | 67.0 | 75.6 | 78.8 | 30.8 | 40.4 |
| ROW 5  | 39.7 | 31.3 | 85.2 | 82.1 | 64.0 | 64.6 | 74.5 | 77.7 | 34.7 | 37.5 |
| ROW 6  | 41.7 | 40.4 | 30.6 | 28.8 | 30.8 | 31.8 | 28.7 | 31.5 | 39.2 | 40.2 |
| ROW 7  | 38.7 | 38.1 | 50.0 | 49.0 | 44.5 | 44.6 | 49.9 | 50.6 | 38.1 | 40.4 |
| ROW 8  | 40.0 | 39.5 | 53.9 | 53.2 | 47.7 | 47.9 | 53.4 | 54.1 | 39.0 | 40.2 |
| ROW 9  | 40.0 | 39.5 | 38.4 | 39.4 | 40.8 | 39.2 | 38.7 | 37.9 | 39.3 | 39.0 |
| ROW 10 | 40.0 | 41.1 | 40.6 | 40.0 | 39.4 | 38.7 | 40.1 | 41.5 | 40.0 | 39.2 |

Figure 6:
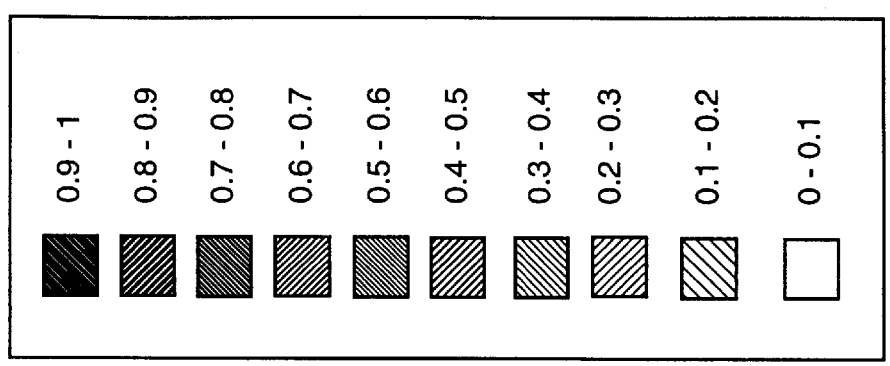
FIG. 6 is a normalized, 3-dimensional plot of enhanced matrix MATRIX_7 provided in the example.
Figure 6:
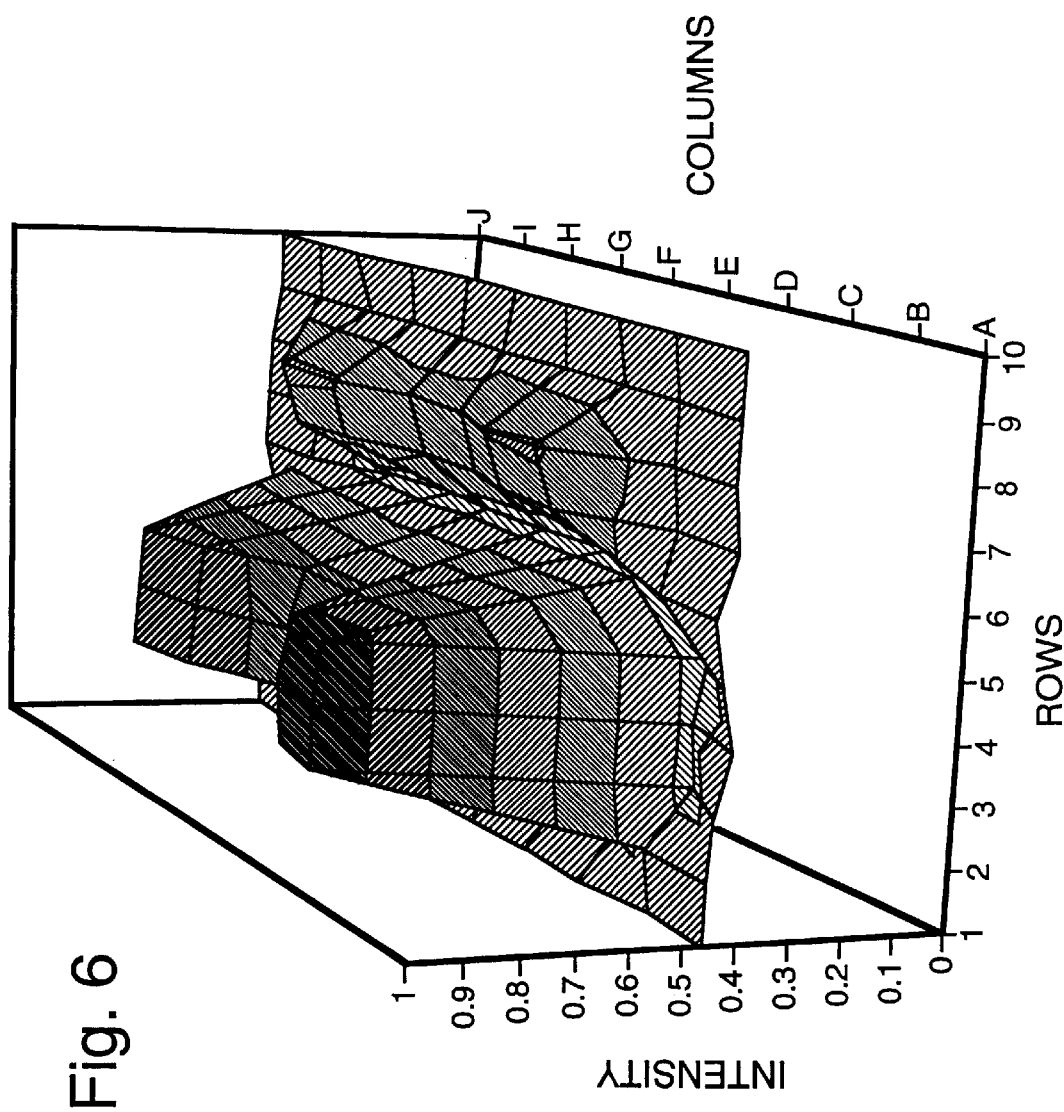

A normalized, 3-dimensional plot of MATRIX_7 is shown in FIG. 6. A comparison of FIG. 5 and FIG. 6 shows how FIG. 6 compresses the range of data so that features formerly in the 0.4–0.5 range on the normalized scale in FIG. 5, now appear in the 0.6–0.7 range in FIG. 6, whereas the features in the 0.9 to 1.0 range remain in the 0.9–1.0 range in both figures. Thus, rather than further increasing the intensity of the high-intensity features in trying to increase the intensity of the low-intensity features, this method maintains the contrast between feature and background for both initially high-intensity and initially low-intensity features. It should be noted here that as an illustrative tool, the plots shown in FIG. 5 and FIG. 6 arbitrarily show variations in gray-scale to indicate different intensity levels, but this variation in no way approximates the gray-scale typical in an actual radiograph.

Those skilled in the art having the benefit of the above description can make numerous modifications particularly as to the actual numerical values used in the examples given above. Any such modifications are to be construed as encompassed within the scope of the invention as claimed herein below.

What is claimed:

1. A method for displaying on a display medium an image corresponding to detected exposures to radiation of a plurality of sensors in an array, the detected exposures converted to a starting matrix having n rows and m columns of digital values, each digital value representing an optical density, the method comprising the steps of:
   (a) creating a weighted, smoothed, subtracted matrix by:
      (a1) sampling the starting matrix to generate a sampled submatrix having n/I rows and m/I' columns of submatrix digital values, wherein I and I' are integers greater than 1;
      (a2) creating a subtracted submatrix by subtracting each submatrix digital value in the sampled submatrix or in a first intervening submatrix from a reference digital value greater than each submatrix digital value;
      (a3) expanding the subtracted submatrix or a second intervening submatrix by extrapolation, interpolation, or both, to create an expanded matrix having n rows and m columns;
      (a4) performing a smoothing step between step (a1) and step (a3); and
      (a5) performing a weighting step sometime after step (a1);
   (b) adding the weighted, smoothed, subtracted matrix to the starting matrix to produce an enhanced matrix;
   (c) using the digital values from the enhanced matrix to display an image.

2. The method according to claim 1 wherein step (a4) comprises applying a smoothing filter to the rows of the sampled submatrix or the subtracted submatrix to create a row-smoothed submatrix, applying a smoothing filter to the columns of the sampled submatrix or the subtracted submatrix to create a column-smoothed submatrix, and then adding the row-smoothed submatrix and the column-smoothed submatrix.

3. The method according to claim 1 wherein I is equal to I'.

4. The method according to claim 1 further comprising expanding the subtracted submatrix or second intervening submatrix in step (a3) by inserting interpolated digital values between each of the digital values in the n/I rows and m/I' columns.

5. The method according to claim 1 wherein the interpolation in step (a3) comprises bilinear interpolation.

6. The method according to claim 1 further comprising in step (c) normalizing the enhanced matrix, mapping the normalized, enhanced matrix onto a look up table to create a matrix of digital display values, and sending the matrix of digital display values to a display medium for displaying an image.

7. The method of claim 1 further comprising reducing the dynamic range the digital values in one of: the sampled submatrix in step (a1), the enhanced matrix in step (b), or both; wherein reducing the dynamic range comprises reducing the dynamic range in one of: an upper range of the data values, a lower range of the data values, or both.

8. The method according to claim 1 wherein step (a5) is performed after step (a3).

9. A method for displaying on a display medium an image corresponding to detected exposures to radiation of a plurality of sensors in an array, the detected exposures converted to a starting matrix (MATRIX_0) having n rows and m columns of digital values, each digital value representing an optical density, the method comprising the steps of:
  (a) creating a weighted, smoothed, subtracted matrix by the steps of:
    (i) sampling starting matrix MATRIX_0 to create a sampled submatrix having n/I rows and m/I' columns, wherein I and I' are integers, and then creating a maximum-limited, sampled submatrix by replacing any digital values in the sampled submatrix greater than a predetermined maximum value with the predetermined maximum value;
    (ii) compiling a row-smoothed submatrix (MATRIX_1) by applying a linear smoothing filter to the digital values along the rows of the maximum-limited, sampled submatrix;
    (iii) compiling a column-smoothed submatrix (MATRIX_2), by applying a linear smoothing filter to the digital values along the columns in the maximum-limited, sampled submatrix;
    (iv) creating a row-column-smoothed submatrix (MATRIX_3) by adding together MATRIX_1 and MATRIX_2;
    (v) creating a subtracted, smoothed submatrix (MATRIX_4) by subtracting each value in MATRIX_3 from a fixed value larger than each value in MATRIX_3; and
    (vi) multiplying each value in MATRIX_4 by a weighing factor to created a weighted, smoothed, subtracted submatrix; and
    (vii) expanding the weighted, smoothed, subtracted submatrix by extrapolation, interepolation, or both, to create the weighted, smoothed, subtracted matrix;
  (b) adding the weighted, smoothed, subtracted matrix to the starting matrix to produce an enhanced matrix; and
  (c) using the digital values from the enhanced matrix to display an image.

10. The method of claim 9 further comprising selecting an anchor point, in step (a)(i) setting the predetermined maximum value equal to a first constant $k_1$ times the anchor point, and in step (a)(v) setting the fixed value equal to a second constant $k_2$ times the anchor point.

11. The method of claim 10 further comprising developing a histogram corresponding to a frequency of occurrence for each digital value in the matrix of digital values, identifying a range of useful data within the histogram, calculating a statistical mode of the useful data within the histogram, and selecting as the anchor point the lesser of: the statistical mode or a pre-selected safety point.

12. The method of claim 10 further comprising developing a histogram corresponding to a frequency of occurrence for each digital value in the matrix of digital values, identifying a range of useful data within the histogram, calculating a statistical mode of the useful data within the histogram, and selecting the statistical mode as the anchor point.

13. The method of claim 12 further comprising reducing the histogram prior to identifying the range of useful data within the histogram.

14. The method of claim 13 further comprising smoothing the histogram prior to calculating the statistical mode.

15. A method for displaying on a display medium an image corresponding to detected exposures of a plurality of sensors, the method comprising the steps of:
  a) creating and storing in a data bank a starting matrix (MATRIX_0) of digital values each representing an optical density corresponding to the detected exposures, the starting matrix having n rows and m columns;
  b) developing a histogram corresponding to a frequency of occurrence of each digital value and calculating a statistical mode (MODE) of at least a portion of data within the histogram;
  c) creating a sampled submatrix of digital values having n/I rows and m/I columns by selecting every $I^{th}$ digital value in the starting matrix, I being an integer;
  d) creating a maximum-limited, sampled submatrix having n/I rows and m/I columns by replacing any digital values in the sampled submatrix greater than a predetermined maximum value with the predetermined maximum value, the predetermined maximum value equal to a constant $k_1$ times the statistical mode (MODE);
  e) compiling a row-smoothed submatrix (MATRIX_1) by applying a linear smoothing filter to the digital values along the rows of the maximum-limited, sampled submatrix;
  f) compiling a column-smoothed submatrix (MATRIX_2), by applying a linear smoothing filter to the digital values along the columns in the maximum-limited, sampled submatrix;
  g) creating a row-column-smoothed submatrix (MATRIX_3) by adding together the row-smoothed submatrix (MATRIX_1) and the column-smoothed submatrix (MATRIX_2);
  h) creating an subtracted, smoothed submatrix (MATRIX_4) by subtracting each value in the row-column-smoothed submatrix (MATRIX_3) from a fixed value equal to a constant $k_2$ times the statistical mode (MODE); and
  i) multiplying each value. in the subtracted, smoothed submatrix (MATRIX_4) by a weighing factor w to create a weighted, smoothed, subtracted submatrix (MATRIX_5) having n/I rows and m/I columns;
  j) creating a weighted, smoothed, subtracted matrix (MATRIX_6) having n rows and m columns by bilinear interpolation of the digital values in the n/I rows and m/I columns of the weighted, smoothed, subtracted submatrix;
  k) adding the weighted, smoothed, subtracted matrix (MATRIX_6) to the starting matrix (MATRIX_0) to create an enhanced matrix (MATRIX_7); and
  l) normalizing the enhanced matrix (MATRIX_7) and mapping the normalized, enhanced matrix onto a look up table comprising a gray scale transfer function to create a matrix of digital display values, and sending the digital display values to the display medium.

16. The method of claim 15 wherein the starting matrix (MATRIX_0) comprises a plurality of 14-bit digital values and step (a) comprises converting each 14-bit digital value in the starting matrix to a 12-bit, logarithmic digital value, developing the histogram corresponding to the frequency of occurrence of each 12-bit, logarithmic digital value, reducing the histogram by partitioning the histogram into bins of sequential 12-bit, logarithmic digital values, identifying a range of useful data within the histogram, smoothing the histogram, calculating a 12-bit, logarithmic, binned statistical mode of the useful data within the histogram, and converting the 12-bit, logarithmic, binned statistical mode to a 14-bit, non-logarithmic, non-binned converted value to be used as the statistical mode (MODE).

17. The method of claim 15 wherein $k_1$ is equal to about 5 and $k_2$ is equal to about 2.

18. A program storage device readable by machine, tangibly embodying a program of instructions executable by the machine to perform a set of method steps for displaying on a display medium an image corresponding to detected exposures to radiation of a plurality of sensors, the detected exposures converted to a starting matrix having n rows and m columns of digital values stored in the program storage device, each digital value representing an optical density, the method steps comprising:
   (a) creating a weighted, smoothed, subtracted matrix by:
      (a1) sampling the starting matrix to generate a sampled submatrix having n/I rows and m/I' columns of submatrix digital values, wherein I and I' are integers greater than 1;
      (a2) creating a subtracted submatrix by subtracting each submatrix digital value in the sampled submatrix or a first intervening submatrix from a reference digital value greater than each submatrix digital value;
      (a3) expanding the subtracted submatrix or a second intervening submatrix by extrapolation, interpolation, or both, to create an expanded matrix having n rows and m columns;
      (a4) performing a smoothing operation between step (a1) and step (a3); and
      (a5) performing a weighting operation sometime after step (a1), optionally after step (a3);
   (b) adding the weighted, smoothed, subtracted matrix to the starting matrix to produce an enhanced matrix;
   (c) using the digital values from the enhanced matrix to display an image.

19. A digital x-ray image data capture system comprising: the program storage device of claim 18;
   a source of penetrative radiation for emitting an unmodulated radiation beam along a path;
   a plurality of sensors in an array of n rows and m columns positioned in the beam path for receiving and detecting exposure to at least a modulated radiation beam derived from said unmodulated radiation beam, each sensor adapted to produce a sensor output proportional to the detected exposure;
   an analog-to-digital converter adapted to receive the sensor output, convert the sensor output to a digital value, and transmit the digital value to the program storage device.

20. The digital x-ray image data capture system of claim 19 further comprising a portion of anatomy placed in the path of said unmodulated radiation beam between said source and said array of sensors, said anatomy capable of modulating said radiation beam to produce said modulated beam.

21. A method for displaying on a display medium a radiographic image of a portion of anatomy corresponding to detected exposures to radiation of a plurality of sensors in an array, the method comprising the steps of:
   a) providing a digital x-ray image data capture system comprising:
      a source of penetrative radiation for emitting an unmodulated radiation beam along a path;
      the plurality of sensors in the array, the array having n rows and m columns, the plurality of sensors positioned in the beam path;
      an analog-to-digital converter for receiving the sensor outputs, converting the outputs to digital values, and transmitting the digital values;
      a program storage device tangibly embodying a program of instructions and for receiving and storing the digital values;
      a program execution machine for reading the program storage device and executing the program of instructions;
   b) placing the portion of anatomy in the path of the unmodulated radiation beam between the source and the array of sensors;
   c) modulating the unmodulated radiation beam into a modulated beam as the beam penetrates the portion of anatomy;
   d) receiving and detecting exposure to the modulated beam with the sensors and producing a sensor output proportional to the detected exposure;
   e) receiving the sensor output in the analog-to-digital converter, converting the sensor outputs to the digital values, each digital value representing an optical density, and transmitting the digital values to the program storage device to be stored in a starting matrix having n rows and m columns; and
   f) the program execution machine modifying the digital values by:
      (i) creating a weighted, smoothed, subtracted matrix from the starting matrix,
      (ii) adding the weighted, smoothed, subtracted matrix to the starting matrix to produce an enhanced matrix; and
      (iii) using the digital values from the enhanced matrix to display the radiographic image of the portion of anatomy.

22. A method for displaying on a display medium an image corresponding to detected exposures to radiation of a plurality of sensors in an array, the detected exposures converted to a starting matrix having n rows and m columns of digital values, each digital value representing an optical density, the method comprising the steps of:
   (a) creating a weighted, smoothed, subtracted matrix by:
      (a1) sampling the starting matrix to generate a sampled submatrix having n/I rows and m/I' columns of sampled digital values, wherein I and I' are integers;
      (a2) filtering said sampled submatrix with a smoothing filter to obtain a smoothed submatrix having filtered digital values;
      (a3) creating a smoothed, subtracted submatrix by subtracting each of said submatrix digital values from a reference digital value; and
      (a4) expanding the smoothed, subtracted submatrix by extrapolating the subtracted digital values to create a smoothed, subtracted matrix having n rows and m columns;
   (b) adding the weighted, smoothed, subtracted matrix to the starting matrix to produce an enhanced matrix;
   (c) using the digital values from the enhanced matrix to display an image; and
   (d) reducing the dynamic range of the digital values in one of: the sampled submatrix in step (a1), the enhanced matrix in step (b), or both; wherein reducing the dynamic range comprises reducing the dynamic range in one of: an upper range of the data values, a lower range of the data values, or both.

* * * * *